Figure 1:
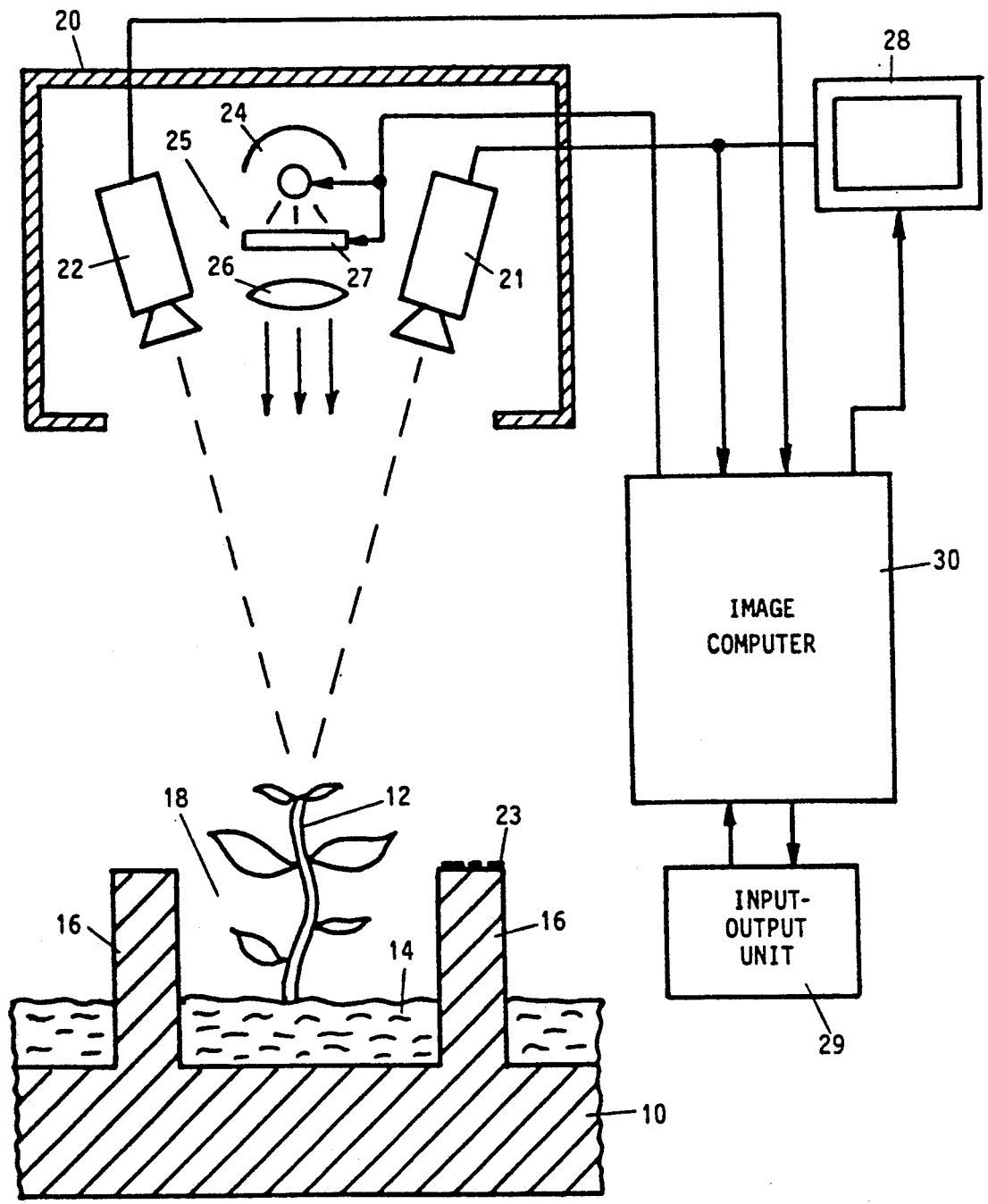

United States Patent [19]

Massen

[11] Patent Number: 5,253,302
[45] Date of Patent: Oct. 12, 1993

[54] METHOD AND ARRANGEMENT FOR AUTOMATIC OPTICAL CLASSIFICATION OF PLANTS

[76] Inventor: Robert Massen, Kämpfenstrasse 39, 7760 Radolfzell, Fed. Rep. of Germany

[21] Appl. No.: 998,760
[22] Filed: Dec. 30, 1992

Related U.S. Application Data

[63] Continuation of Ser. No. 601,770, Oct. 26, 1990, abandoned.

[30] Foreign Application Priority Data

Feb. 28, 1989 [DE] Fed. Rep. of Germany ....... 3906215

[51] Int. Cl.$^5$ .................... G06K 9/00; G06K 9/34; H04N 13/00
[52] U.S. Cl. .......................................... 382/1; 382/9; 382/17; 358/88; 358/109
[58] Field of Search .................... 382/1, 9, 17, 25; 209/580, 939; 356/12, 402; 358/88, 107, 108, 109

[56] References Cited

U.S. PATENT DOCUMENTS

| | | | |
|---|---|---|---|
| 3,748,471 | 7/1973 | Ross et al. | 250/333 |
| 4,015,366 | 4/1977 | Hall, III | 47/1 R |
| 4,146,926 | 3/1979 | Clerget et al. | 364/556 |
| 4,341,466 | 7/1982 | Dyregrov | 355/50 |
| 4,528,587 | 7/1985 | Jones, Jr. | 358/92 |
| 4,532,757 | 8/1985 | Tutle | 56/328 R |
| 4,573,191 | 2/1986 | Kidode et al. | 382/1 |
| 4,625,329 | 11/1986 | Ishikawa et al. | 382/1 |
| 4,656,594 | 4/1987 | Ledley | 364/498 |
| 4,665,036 | 5/1987 | Dedden et al. | 435/301 |
| 4,741,042 | 4/1988 | Throop et al. | 382/1 |
| 4,814,077 | 4/1989 | Kikuchi et al. | 358/98 |
| 5,020,675 | 6/1991 | Cowlin et al. | 209/538 |
| 5,085,325 | 2/1992 | Jones et al. | 209/580 |

FOREIGN PATENT DOCUMENTS

| | | |
|---|---|---|
| 0247016 | 11/1987 | European Pat. Off. ............ 209/580 |
| 0146476 | 6/1988 | European Pat. Off. . |
| 2739679 | 3/1978 | Fed. Rep. of Germany . |
| 3420760 | 12/1985 | Fed. Rep. of Germany . |
| 3639636 | 11/1986 | Fed. Rep. of Germany . |
| 2599579 | 12/1987 | France . |
| 0222981 | 11/1985 | Japan .................... 382/17 |
| 1473537 | 6/1974 | United Kingdom . |
| 1494357 | 12/1977 | United Kingdom . |
| 84/01875 | 5/1984 | World Int. Prop. O. . |
| 86/06854 | 11/1986 | World Int. Prop. O. . |

OTHER PUBLICATIONS

Deleplanque et al., "An Intelligent Robotic System for In Vitro Plantlet Production", Proc. of the 5th Int. Conf. on Robot Vision and Sensory Controls, Oct., 1985, pp. 305-313.

Malloch et al., "A Class of Adaptive Model- and Object-Driven Nonuniform Sampling Methods for 3-D Inspection", *Machine Vision and Applications*, 1988, pp. 97-114.

Article "Real-time grey level and color image pre-processing for a vision guide biotechnology robot" by R. C. Massen, P. Buttcher and U. Leisinger, published in the Proceedings of the 7th International Conference on Robot Vision and Sensory Controls ("RoViSeC-7"), Feb. 2-4, 1988, Zurich, Switzerland, pp. 115 to 122.

*Primary Examiner*—David K. Moore
*Assistant Examiner*—Andrew W. Johns
*Attorney, Agent, or Firm*—Sixbey, Friedman, Leedom & Ferguson

[57] ABSTRACT

For automatic optical classification of plants an image of in each case one plant is captured by a color video camera. The color video signals furnished by the color video camera are digitized and classified pixelwise in predetermined color classes which are associated on the one hand with the image of the plant and on the other hand with the image of the background. A digitized image of the plant designated by the color classes is stored in an image memory and evaluated by an image computer for classification of the plant. The segmentation of the image of the plant from the image of the background is carried out on the basis of the allocation of the pixels to the predetermined color classes and from the segmented image of the plant geometrical form features and color features are determined. Furthermore, the height of the plant is determined, for which purpose possibly two video cameras and a light pattern projector are employed. The color classifier used for color classification is configured so that it can learn the predetermined color classes by presentation of image fragments.

22 Claims, 5 Drawing Sheets

METHOD AND ARRANGEMENT FOR AUTOMATIC OPTICAL CLASSIFICATION OF PLANTS

This application is a continuation of Ser. No. 07/601,770, filed Oct. 26, 1990, now abandoned.

The invention relates to a method for automatic optical classification of plants in which by a video camera an image of in each case one plant is acquired, the video signals of the acquired image furnished by the video camera digitized pixelwise, a digitized image of the plant stored in an image memory and the stored digitized image evaluated by an image computer for classification of the plant.

In the cultivation of new species of plants, the random sample checking of seed batches and biological experiments, plantlets are grown in large numbers under defined climatic conditions. The growth is optically checked several times and assessed on the basis of visual features. For this human assessment purely qualitative properties are used because there are hardly any measuring methods for determining the characteristics important for the plant growth on living plants without destruction. The visual assessment of seedlings, which frequently grow on nutrient media or filter paper impregnated with nutrient solution under strictly controlled conditions, is an important working step in the research of new species and the growing of high-quality plantlets.

Apart from the lack of reliable quantitative measurement data, the visual assessment by humans is time-consuming and cost-intensive. The process-accompanying data acquisition, automatic evalution and direct control of the ambient conditions is possible only to a very limited extent because the human assessment furnishes above all qualitative but hardly quantitative data. Since in growth tests numerous plantlets do not germinate or germinate only inadequately, these cases are discovered late. Valuable growth space remains unutilized. Poorly growing plantlets demand greenhouse resources and thus represent a substantial cost factor which can be substantially reduced by early detection of these plantlets and replacement by properly growing ones. The automatic quantitative classification of plantlets is thus an important step not only in experimental growth tests but also in the series cultivation of plantlets, with the aim of obtaining automatable agricultural operations with an optimized cultivation programme and accompanying quality control.

A method for automatic optical classification of plants of the type set forth at the beginning is already known from the "Proceedings of the 5th International Conference on Robot Vision and Sensory Controls", Oct. 29-31, 1985, Amsterdam, pages 305 to 313. In this known method, with the aid of a black-and-white video camera directed perpendicularly from above onto the plant a grey value picture of the plant is compiled, the image of the plant segmented from the background by binarizing and the total area of the image regions of the binary value associated with the plant determined. This total area is then output as a characteristic quantity proportional to the organic mass of the plant.

This method represents a first step towards a quantitative assessment of plants but it proves to be insufficient. For the exact assessment of plantlets requires far more detailed knowledge not only on the total amount of organic mass but also on the form of the plant growth (number of leaves, shape of the leaves, etc.), the coloring of individual plant zones (leaf tips, stems, etc.) and above all the plant height. Since plantlets are usually cultivated in densely packed containers with up to 2000 plantlets per $m^2$, it is not possible to obtain side images of individual plants. The exact optical height measurement of plants with simple means has so far not been solved.

An essential problem in this known method further resides in that it is frequently not possible on the basis of brightness differences alone to clearly segment the image of the plant, i.e. distinguish it from the image of the background. The plants grow on very different nutrient media, the brightness of which frequently does not differ enough from the brightness of the plant parts which in turn often have very different brightness values. As a result, erroneous assessments are frequently made.

The problem underlying the invention is to provide a method of this type which gives a clear segmentation of the image of the plant and permits the determination of form and color features as well as the determination of the height of the plant.

This problem is solved according to the invention in that the image of a plant is captured by a color video camera, that the digitized color video signals prior to storing of the digitized image are classified pixelwise in accordance with predetermined color classes which are assigned on the one hand to the image of the plant and on the other to the image of the background, that the segmentation of the image of the plant from the image of the background is effected on the basis of the allocation of the pixels to the predetermined color classes, that from the segmented image of the plant geometrical form features are determined and that the form features determined are evaluated for derivation of a quality measure.

The color classification by predetermined color classes used in the method according to the invention permits in all cases a clear segmenting of the image of the plant because the color classes for each plant species and for each background (nutrient medium) can be predefined so that the image of the plant can clearly be distinguished from the background. This makes it possible to determine geometrical form features, such as number of the leaves, area and circumference of the leaves, angle between the leaves, etc., and use them to derive the quality measure. By assigning different color classes to different plant parts it is moreover possible to determine from the digitized and stored image also color features of the plants and incorporate them into the derivation of the quality measure.

A particularly advantageous further development of the method according to the invention resides in that the color classifier learns the color classes by showing image fragments in an interactive training phase. This training phase does not require any knowledge of digital image processing or programming and consequently can be carried out by semiskilled personnel.

The plant height can be determined from the image of the plant acquired by a video camera for example by the light section method. Another method of determining the plant height according to the invention resides in that by two video cameras spaced apart from each other two stereo images of the plant are acquired and that the digitized stereo images stored in image memories are evaluated by the image computer for determining the height of the plant. In both cases, in accordance with the invention the determination of the plant height is facilitated in that during the image acquisition a light pattern is projected onto the plant.

Advantageous further developments of the method according to the invention and arrangements for carrying out the method are characterized in the subsidiary claims.

Figure 2:
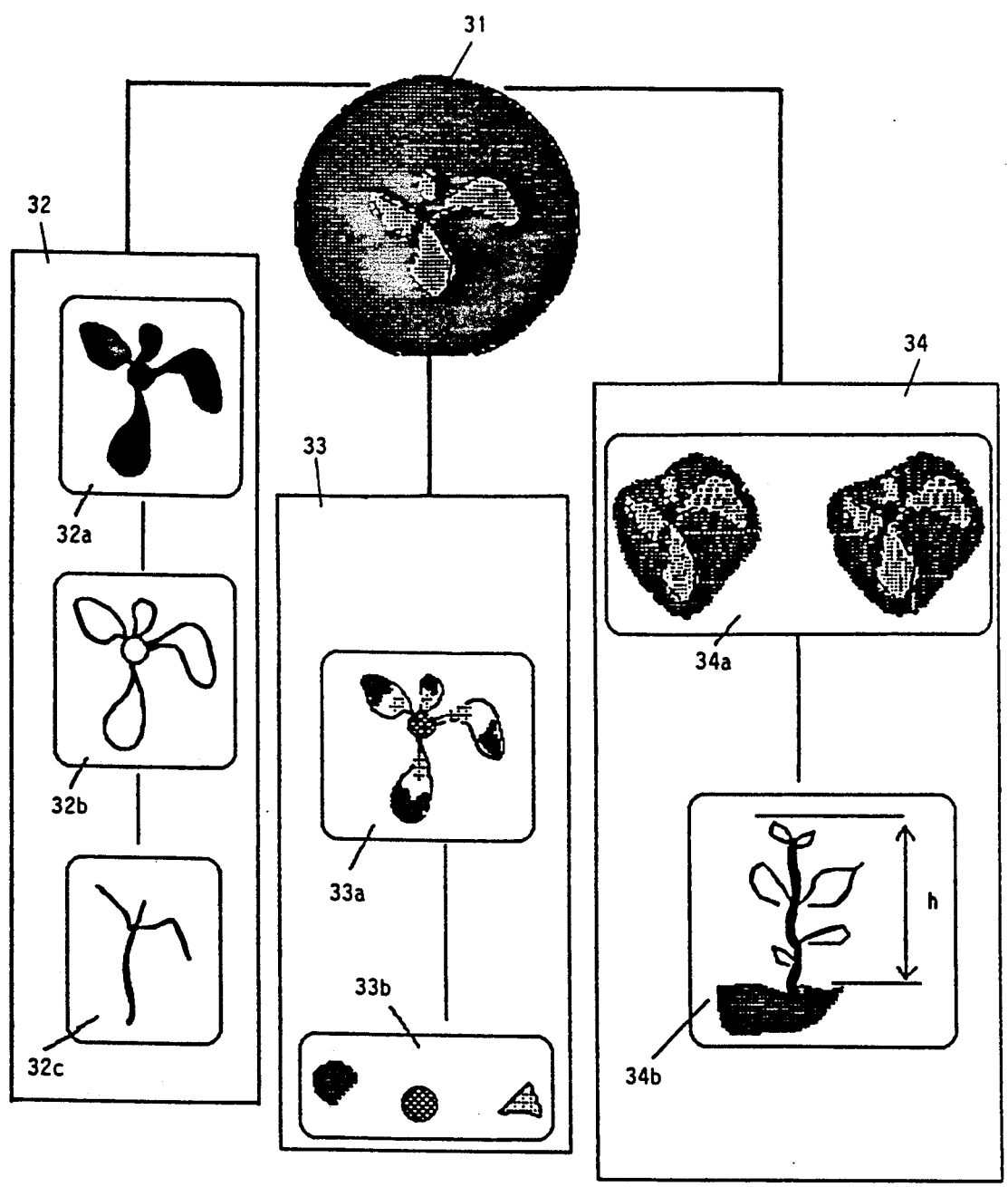
Figure 3:
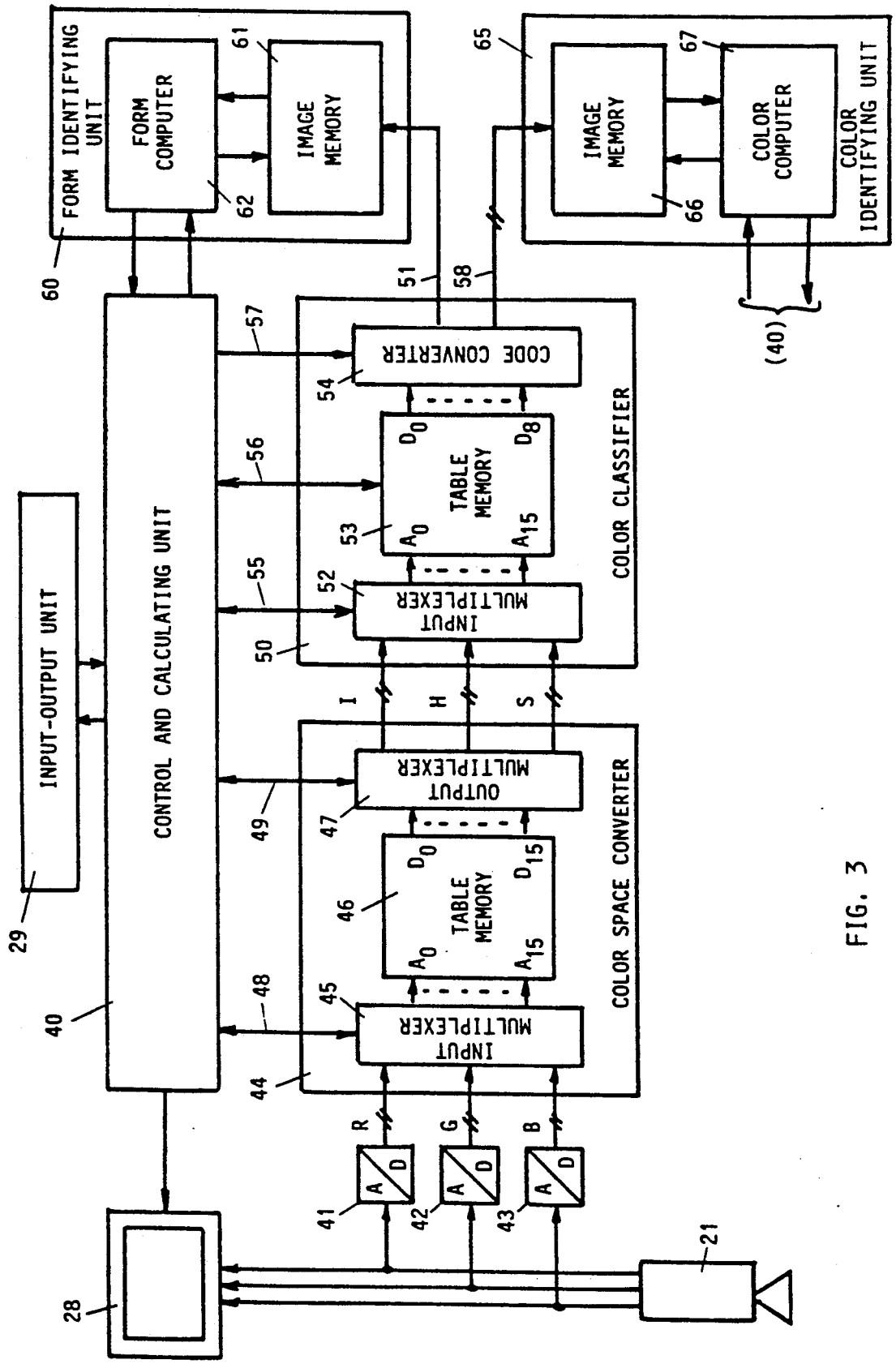
Figure 4:
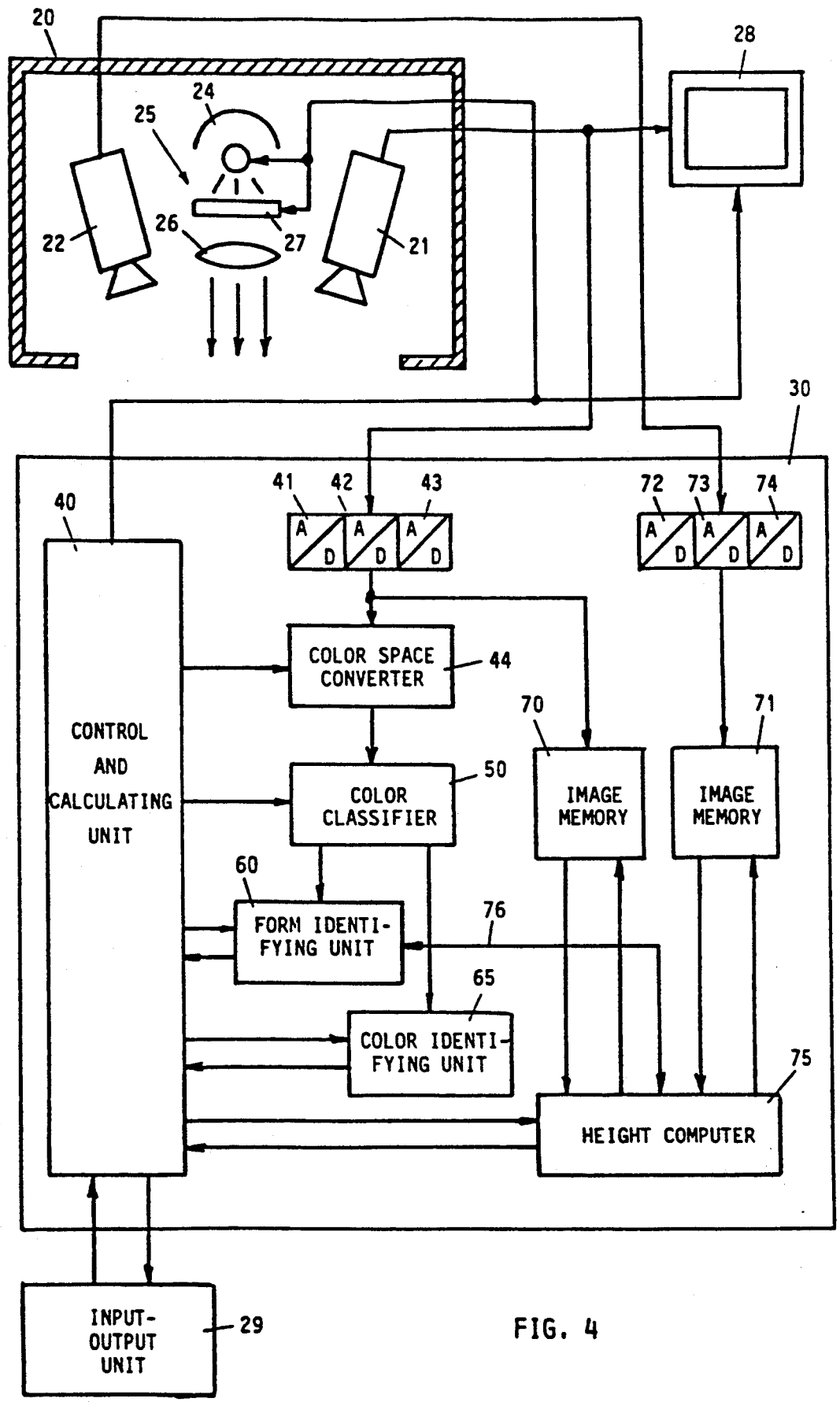
Figure 5:
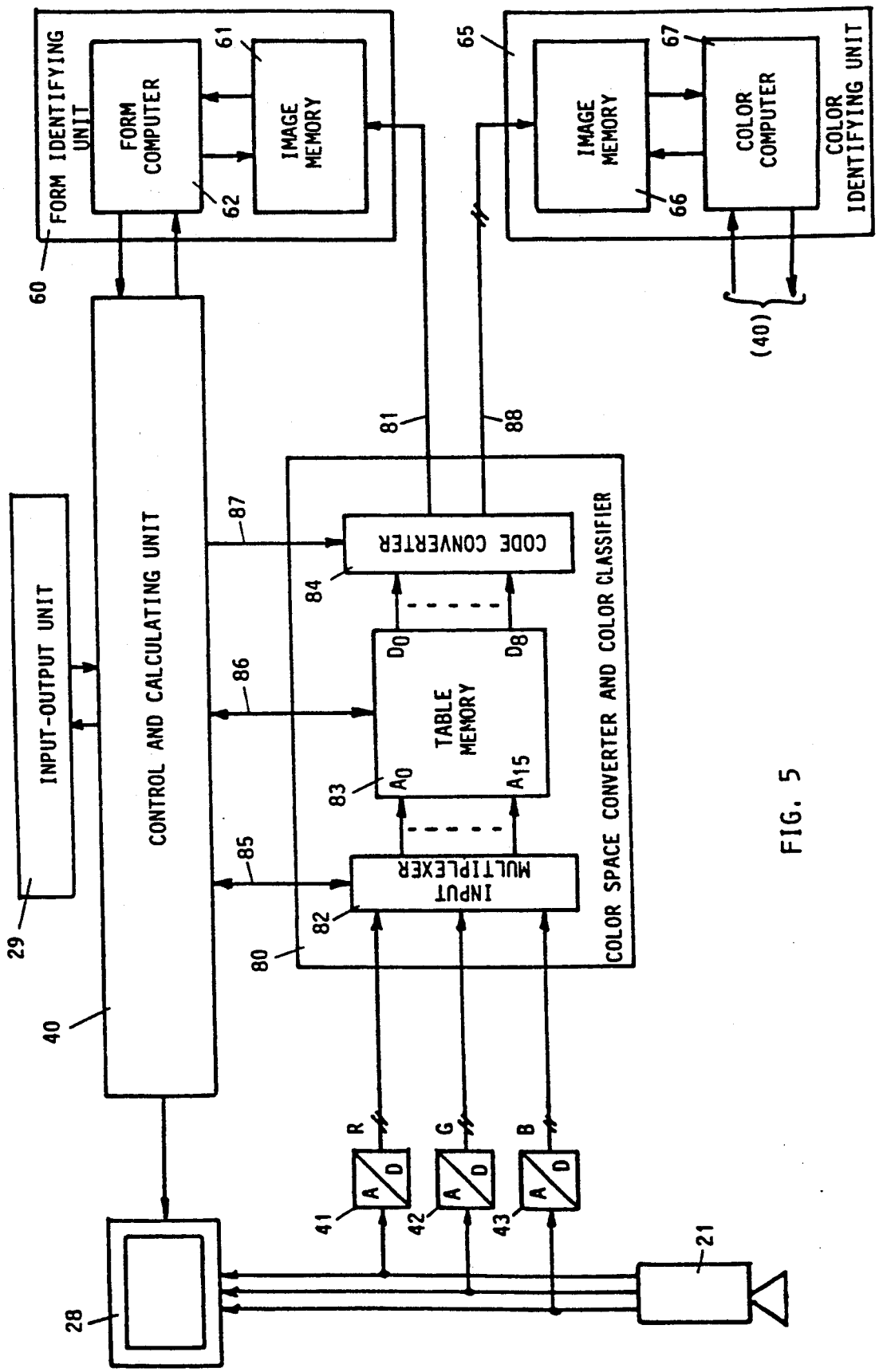

Further features and advantages of the invention will be apparent from the following description of examples of embodiment with the aid of the drawings, wherein:

FIG. 1 shows a schematic illustration of an arrangement for automatic optical classification of plants, FIG. 2 shows in sketch form the determination of form features, color features and the height of the plants with the arrangement of FIG. 1, FIG. 3 shows the components of the image computer employed to determine form features and colour features, FIG. 4 is a block diagram of the image computer in the arrangement of FIG. 1 and FIG. 5 shows a modified embodiment of the circuit components of FIG. 3.

FIG. 1 shows schematically a sectional view of a container 10 in which the plants 12 to be investigated are growing on a nutrient medium 14. The container 10 can be divided by partitions 16 into compartments 18, each compartment 18 containing a plant 12. Above the container 10 a measuring head 20 is arranged which contains two color video cameras 21 and 22 which are arranged at a defined distance apart and each of which can capture an image of a plant at a known angle with respect to the vertical. The container 10 and the measuring head 20 are adjustable relatively to each other in such a manner that in succession each plant 12 can be brought into the field of view of the two color video cameras 21 and 22. For this purpose, for example, the measuring head 20 can be movable in two coordinate directions over the stationary container 10 or the container 10 can be movable in two coordinate directions beneath the stationary measuring head 20. Furthermore, composite movements are possible by moving the container 10 in one direction beneath the measuring head 20 whilst the measuring head 20 is moved transversely of the movement direction of the container 10. To enable each plant 12 in the container 10 to be uniquely identified, on the upper sides of the partitions 16 codes 23, for example in the form of bar codes, may be provided which are readable with the aid of the measuring head 20 and for example indicate the coordinates of each plant in the container.

The measuring head 20 further includes an illuminating means 24 with which the particular plant 12 captured by the color video cameras 21, 22 can be illuminated from above. The illuminating means 24 may be implemented by a constant light source or by a pulsed light source. With the aid of the illuminating means 24 and a light pattern projector 25 having a projection lens 26 and a light pattern generator 27, it is further possible to project a light pattern furnished by the light pattern generator 27 onto the plant 12. The light pattern generator 27 may for example be an electronically controllable light modulator. A known example of an electronically controllable light modulator is a liquid crystal display (LCD). Instead of an electronically controllable light modulator, a transparency movable by a motor under program control and having different impressed projection patterns may be used in the manner of a diapositive.

The purpose of the projection of a light pattern onto the plant will be explained later.

The color video cameras 21 and 22 may be usual commercially available television or video cameras which convert the image of the plants to electrical video signals which are suitable for the reproduction of a color image. Preferably, each color video camera is formed by a CCD matrix camera. Each color video camera furnishes at three outputs three color signals which represent the component colors in the basic colors red, green and blue. The combination of these three color signals, following the usual terminology, is referred to hereinafter as "RGB signals".

The RGB video signals furnished by the color video camera 21 are supplied to a monitor 28 on which the image acquired is made visible. Furthermore, the RGB signals furnished by the two color video cameras 21 and 22 are supplied to an image computer 30 which evaluates these signals to detect the plant 12 automatically with respect to the background (the so-called "segmentation"), to determine quantitative form features and perform a color classification of the plant parts. The plant is here classified and evaluated simultaneously by the features:

geometrical form
color
height.

The image computer 30 also supplies control signals to the light pattern generator 27 and to the monitor 28. Via an input-output unit 29 the connection is established between the image computer 30 and the user as well as with any higher-ranking host computer which may be present.

FIG. 2 shows schematically how the images acquired by the color video cameras 21 and 22 are processed by the image computer 30 in three channels. A form channel 32 serves for classification and evaluation of features of the geometrical shape or form, a color channel 33 for classification and evaluation of color features and a height channel 34 for determination of the height of the plant. The methods for determining these three feature classes with the aid of the measuring head 20 and of the image computer 30 will be described in more detail hereinafter.

1. Classification and evaluation of the geometrical form

For the classification and evaluation of the geometrical form of the plant the image of the latter must be clearly distinguished from the image of the background. This process is referred to as "segmenting". The color of the nutrient medium 14 on which the plant is growing can vary from white (in the case of paper nutrient media) through yellow (agar media) to dark brown (peat mixtures). The containers 10 are frequently made from white plastic, for example Styrofoam, and due to soiling the brightness contrast between plant and background may be very small. Thus, a clear distinction between plant and background cannot be effected through brightness differences alone. For this reason, in the image computer 30 the segmenting is carried out by a pixelwise color classification in the color space. FIG. 3 shows the block diagram of the components of the image computer 30 used for this purpose.

The color video camera 21 furnishes at three outputs three analog color signals. i.e. the red signal R, the green signal G and the blue signal B, of the captured color image. These three color signals are supplied to the monitor 28 which also receives control signals from a control and calculating unit 40 contained in the image computer 30. Furthermore, to each of the three outputs of the color video camera 21 an analog-digital converter 41, 42 and 43 respectively is connected which converts the color signal supplied to it pixelwise to a digital signal. For each image point (pixel) of the acquired color image a digital code group therefore appears in real time at the output of each of the three analog-digital converters 41, 42, 43 and represents the intensity of the associated color value with a quantization defined by the digit number of the code group. With regard to the following further processing the quantization of the red signal R and the blue signal B is made for example in each case with 5 bits, i.e. in 32 steps, and the quantization of the green signal G with 6 bits, i.e. in 64 steps, so that the entire RGB color information of a pixel is represented by a 16 bit word. The 16 bits of the 16 bit words belonging to the consecutively scanned pixels appear in pixel clock rate (e.g. 15 MHz) in each case simultaneously at five parallel outputs of the analog-digital converter 41, at six parallel outputs of the analog-digital converter 42 and at five parallel outputs of the analog-digital converter 43.

Connected to the 16 outputs of the analog-digital converters 41, 42 and 43 is a color space converter 44 which converts the digital RGB signal to digital IHS signals, i.e. into three signals representing the intensity I, the hue H and the saturation S. The color image captured by the color video camera is thereby converted from the RGB color space to the IHS color space. The IHS color space is less correlated than the RGB color space and is therefore more suitable for automatic color classification. The IHS color space also corresponds to the manner of observation of a human observer.

The following equations apply for the conversion:

$$I = \frac{R + G + B}{3}$$

$$S = 1 - \frac{3 \cdot \min(R,G,B)}{I}$$

$$H = \frac{\arccos 0.5 \cdot \{[(R - G) + (R - B)]\}}{\sqrt{(R - G)^2 + (R - B) \cdot (G - B)}}$$

For R=G B, S=0 (no color information).

To ensure that the IHS signals appear at the outputs of the color space converter 44 pixelwise in real time, i.e. with the pixel clock rate of 15 MHz, the color space converter is preferably implemented as table computer 50 in which for each of the $2^{16}$ possible combinations of digital RGB signals the associated combination of IHS signals is stored likewise in the form of a 16 bit word. The color space converter 44 contains in this case an input multiplexer 45, a table memory 46 and an output multiplexer 47. The table memory 46 is formed for example by a 64 k×16 bit SRAM. The input multiplexer 45 receives at its inputs the parallel 16 bit words from the outputs of the analog-digital converters 41, 42, 43 and applies each of said 16 bit words as address code to the address inputs $A_0$ to $A_{15}$ of the table memory 46 which thereupon at its data outputs $D_0$ to $D_{15}$ supplies the 16 bit word stored at the respective address to the output mutliplexer 47. Thus, at the 16 outputs of the output multiplexer 47 the IHS signals associated with each pixel appear at the clock rate of the pixel scanning in real time, the intensity I being quantized for example with 5 bits, the hue H with 6 bits and the saturation S with 5 bits. The correct sequence of these functions is controlled by control signals which are furnished by the control and calculating unit 40 via a connection 48 to the input multiplexer 45 and via a connection 49 to the output multiplexer 47.

Connected to the outputs of the color space converter 44 is a color classifier 50 which classifies each incoming IHS signal of a pixel into a previously learned color class or group of color classes and at the output 51 furnishes a signal which indicates to which color class or color class group the color of the pixel represented by the IHS signal belongs. For the investigation of plants there can for example by a color class "green" for leaves, a color class "yellow" for stems and a color class "background" for all other colors. If the IHS signal of a pixel is classified either in the color class "green" or in the color class "yellow", the color classifier 50 emits at the output 51 for this pixel the corresponding class code, for example the binary code symbol "1" for "plant". If the IHS signal is not classified in the color classes associated with the plant, i.e. belongs to the color class "background", the color classifier 50 emits at the output 51 the binary code symbol "0" for "background". The result is still an image made up of pixels but the value associated with each pixel is no longer a color but is a class designation. In this manner the image of the plant may be separated from the background so that the form features can be evaluated.

One problem with this color classification is that the colors of plant parts cannot be associated with a specific point in the three-dimensional IHS color space but exhibit considerable spreads and can thus lie anywhere in a relatively large region of the IHS color space. The green of a leaf of a plant generally has a large range of saturation values; the IHS values associated with the individual pixels of such a leaf thus form a cluster in the three-dimensional IHS color space. Clusters separate from each other are also nothing unusual. The color classifier must thus firstly know which regions of the IHS color space are to be associated with the "plant" and it must secondly be able to classify the IHS signals arriving at pixel clock rate in real time, i.e. determine whether or not the color of the respective pixel lies in a range associated with the "plant".

The color classifier 50 represented in FIG. 3 is so constructed that it
 can be "trained" in simple manner, i.e. can "learn" the color classes associated with the plant or different plants parts;
 after learning the color classes can execute the pixelwise classification with pixel clock rate in real time;
 can carry out both functions with a particularly low circuit expenditure.

For this purpose, the color classifier 50 is constructed in similar manner to the color space converter 44 as table computer. It contains an input multiplexer 52, a table memory 53 formed for example by a 64 k×8 bit SRAM, and a code converter 54. These circuit blocks receive control signals from the control and calculating unit 40 via connections 55, 56 and 57.

In the same manner as in the table memory 46 of the color space converter 44, in the table memory 53 of the color classifier 50 as well each 8 bit memory cell is assigned to a point in the three-dimensional IHS color space. Each 16 bit word furnished by the color space converter 44 is applied via the input multiplexer 52 to the 16 address inputs $A_0$ to $A_{15}$ of the table memory 53, the memory cell allocated to the color of the pixel being transmitted thereby being addressed. When the color classifier 50 has been completely "trained", in each memory cell the class code which has been allocated to the respective color is stored. The read class code appears at the 8 data outputs $D_0$ to $D_8$ and is supplied to the code converter 54 which at the output 51 emits the code symbol "1" for all class codes allocated to the image of the "plant" and the code symbol "0" for all other class codes.

The color classifier 50 has a further output group 58 at which for a purpose which will be explained later more detailed class codes with a greater bit number are emitted for example the complete 8 bit words. The code conversion can be carried out in the simplest manner in that in each 8 bit word a certain bit location indicates by the binary value "1" or "0" whether the respective class code belongs to the image of the plant or to the image of the background. In this case the signals from the data output of the table memory 53 associated with this bit location can simply be transmitted to the output 51.

With the code symbols or code words appearing with pixel clock rate at the outputs 51 and 58 of the color classifier 50 the pixel colors are classified in real time. A requirement for this is of course that in the table memory 53 the correct class code is stored in each memory cell. As has already been mentioned, the allocation and storing of the class codes is by training the color classifier. This training can be carried out in simple manner with the color classifier described by mere showing of typical plant parts in an interactive learning phase (so called "monitored learning"). No special knowledge is necessary to do this and consequently the training can easily be carried out by semiskilled personnel.

To train the color classifier 50, firstly the content of all the memory cells of the table memory 53 is erased. Then, with the aid of the color video camera 21 an image of the plant and of the background is acquired and represented on the monitor 28. With the aid of a marking the user encircles on the screen the image of the plant part to be recognised and allocates a class code to the color of said plant part. For example, the plant part may be a leaf and the allocated class code can be "green". The marked region should have as many as possible components of the color to be detected and as little as possible components of other colors. These operations are carried out under the control of the control and calculating unit 40 of the image computer 30 with the aid of the input/output unit.

In the color converter 44 and in the color classifier 50 only the pixels of the marked image region are evaluated. For each pixel, the IHS color value is determined in the color space converter. The memory cell allocated to said IHS color value is addressed in the table memory 53 and the content of this addressed memory cell is incremented. If all the pixels of the marked image region had exactly the same IHS color value, after the evaluation of this image region the content of a single memory cell would be very large whilst all the other memory cells would be empty. Because of the inevitable variations in intensity, hue and saturation, this case does not of course arise in practice. On the contrary, a range of memory cells is obtained with contents of different sizes, most of which are allocated to IHS color values which are close together in the IHS color space, i.e. form a "cluster". The contents of these memory cells are as it were a histogram of the investigated image area.

The process described is repeated with as many as possible plant parts to obtain a significant cluster formation in the three-dimensional IHS color space. At the end of the training phase the contents of all the memory cells are compared with a threshold value. The previously defined class code is written into the memory cells having contents which have been incremented frequently enough and therefore exceed the threshold value whilst the class code for "background" is entered into all the other memory cells. Preferably, the class code for "background" is also written into all the memory cells assigned to low saturation values because for regions with low color saturation, i.e. which are almost black or almost white, the term "color" is meaningless.

The clusters thus marked are generally not densely populated because it cannot be assumed that during the training phase all the IHS color vectors lying in the interior of such a cluster are also actually encountered in the image regions investigated. It is therefore necessary to close gaps within the clusters to ensure that afterwards, when such color vectors occur in the image evaluation, the respective pixels are correctly classified.

One possibility of filling the clusters is that the clusters are subjected to a three-dimensional dilatation with subsequent erosion. Such methods are known for the case of two-dimensional processing of binary images under the name "morphological image operations" or "fermeture". They are applied here to a three-dimensional table classifier to obtain clear and compact clusters in spite of the always inadequate random test scope.

Another learning method with which compact clusters without gaps can be obtained resides in that in the pixel evaluation not only the content of the address memory cell is incremented but also the contents of the memory cells with adjacent addresses in the IHS color space. For this purpose the content of the memory cell addressed by the IHS color vector is incremented by a constant $K_0$ and the contents of the adjacent memory cells are incremented by a variable K(i) which becomes increasingly smaller with increasing distance from the addressed memory cell. This may for example be done in accordance with the rule $$K(i) = K_0/r^2$$

wherein r is the Euclidean distance of the point allocated to the particular memory cell i to be incremented from the point allocated to the addressed memory cell in the three-dimensional IHS color space. With this learning taking account of the neighbourhood closed clusters without gaps are already obtained in the pixel evaluation, thus obviating the necessity of subsequenty filling of the clusters by three-dimensional dilatation with subsequent erosion. With this method as well, at the end of the learning phase the contents of all the memory cells are compared with a fixed threshold value and in all memory cells having contents which exceed the threshold value the class code denoting the selected color class is entered. This concludes the interactive learning process of the color classifier.

The learning method described does not require any knowledge of programming, code pattern detection or image processing on the part of the user, involving simply the showing of the plant parts to be identified. The training of the color classifier can therefore be carried out by semiskilled personnel.

For plants of different species of course different tables are obtained in the color classifier. As soon as the color classifier has been trained for a specific plant species the table obtained for this plant species can be stored in an external memory and the color classifier can then be trained for another plant species. When later a certain plant species is to be investigated, the associated table need only be loaded into the table memory 53 of the color classifier.

As soon as the table memory 53 of the color classifier 50 has been given the memory content associated with a specific species of plant either by training or by loading a table compiled in an earlier learning operation, any desired number of plants of this plant species can be continuously automatically classified. For each image of a plant captured by the color video camera 21 the color classifier 50 furnishes at the output 51 pixelwise in real time a sequence of binary code symbols "1" or "0", the binary code symbol "1" indicating that the respective pixel belongs to the image of the plant whilst the binary code symbol "0" indicates that the pixel belongs to the image of the background. In this manner the image is binarized, the binarizing taking place however not by intensity stages but by previously learned color classes.

The output 51 of the color classifier 50 is connected to the input of a form or shape identifying unit 60. The form identifying unit 60 includes an image memory 61 containing for each pixel a memory cell of which the address is in a unique relationship to the coordinates of the pixel in the acquired image. The image memory 61 is controlled by the control and calculating unit 40 synchronously with the image scanning so that simultaneously with the scanning of each pixel the associated memory cell in the image memory 61 is addressed. The binary code symbol "1" or "0" appearing for this pixel at the output 51 of the color correlator 50 is written into the addressed memory cell. Thus, after the complete scanning of an image the image binarized by color classes is stored in the image memory 61.

The form identifying unit 60 further contains a form or shape computer 62 which processes the content of the image memory 61 according to a predetermined program to evaluate the geometrical forms of the segmented plant parts. Depending on the use of the apparatus and the type of plants, this evaluation may be very different. For example, geometrical features or form features, such as leaf area, number of leaves, circumference of the leaves, ratio of circumference to area, angle between the leaves, etc., can be calculated. The recognition of the individual leaves can be carried out by following the contours; for this purpose, the binarized image can be converted to a contour image. Furthermore, preferably as simplified graphical description the skeleton of the plants is calculated, from which further structural features, such as the number of leaf tips, symmetry of the plant, etc., can be determined. All these operations can be carried out by methods of image processing known per se (cf. for example: Haberäcker "Digital image processing", Hanser Verlag 1985).

FIG. 2 shows as example schematically a few steps of this digital image processing in the shape or form channel 32: the stage 32a is the binarized image stored in the image memory 61, the stage 32b the contour image and the stage 32c the skeleton of the plant.

The characteristic quantities determined are compared with preset threshold values, thereby achieving a quantitative classification of the plants in quality classes. Since all the characteristic quantities are present as numerical values, by periodic optical surveying of the plants quantitative periodic growth logs can be compiled so that controlling interventions may be made in the growth process in good time by changing the controlling parameters such as temperature, moisture, light cycle, nutrient supply.

2. Classification by color features

Numerous assessment features for the state of a plant relate to the color. The color features cannot be evaluated by the form identifying unit 60 of FIG. 3 because the binarized image stored in the image memory 61 no longer has any color features. For this reason, the image computer 30 comprises a color channel in addition to the form channel. The classification by color features uses extensively the same method steps as the previously described classification by form features so that the same circuit components can be used therefor. This is made clear by FIG. 4 which shows the block circuit diagram of the entire image computer 30 together with the measuring head 20, monitor 28 and the input-output unit 29. The image computer 30 first contains apart from the control and calculating unit 40 the already described components of the form channel, that is the analog-digital converters 41, 42, 43, the color space converter 44, the color classifier 50 and the form identifying unit 60. The color channel also requires analog-digital converters for the RGB signals and a color space converter of the same type as the form channel. It is therefore assumed in FIG. 4 that these components are common to the two channels. Furthermore, the color channel also requires a color classifier which however in contrast to the color classifier of the form channel must permit not only a classification according to two color classes "plant" and "background" but a classification in accordance with several different learned color classes in order to be able to automatically detect differently colored plant parts such as leaves, stems, buds, etc. Since the color classifier 50 described above is constructed so that it also meets this requirement, it is assumed in FIG. 4 that the color classifier 50 is also common to the form channel and the color channel in that the signals furnished at the output 51 are used in the form channel and the signals furnished at the output group 58 are used in the color channel. It would of course also be possible to employ in the color channel a further simultaneously operating color classifier in parallel with the color classifier 50. In each case the training of the color classifier for the color channel is carried out in the previously described manner so that it can classify the successively arriving pixels in accordance with different learned color classes and for each pixel emits a class code designating the color class to which the pixel belongs.

As FIGS. 3 and 4 show, to the output group 58 of the color classifier 50 a color identifying unit 65 is connected which has substantially the same configuration as the form identifying unit 60. As shown in FIG. 3 it also contains an image memory 66 and a color computer 67. In the image memory 66 for each scanned pixel the class code furnished by the color classifier 50 for said pixel is stored. In the image memory 66 after the complete scanning of an image a highly simplified digitized color image of the plant is thus available which has only a few different colors. As example, in FIG. 2 in the color channel 33 at 33a the digitized image of a plant is represented having three color classes, "leaf tips", "stem tips" and "leaf root" as is stored in the image memory 66 of the color identifying unit 65.

The evaluation of the color classes of the digitized color image stored in the image memory 66 may for example be done in that the color computer 67 carries out a quantitative zonewise surveying of the entire area of each of the different color classes. This is represented in FIG. 2 at 33b. The values determined are then compared with the predetermined threshold values, permitting allocation of the plants to quality classes. Thus, the proportion of the plant parts having a learned green color permits the maturity state to be deduced. It is therefore possible for example to measure the adequate germination of seedlings quantitatively and classify such seedlings in growth quality classes.

3. Determination of the plant height

FIG. 4 also shows the components of the image computer 30 which form the height channel serving to determine the plant height. It will be assumed as example that for determining the plant height the stereo triangulation known from photogrammetry is used. In this method, to determine the height corresponding pixels must be found in two stereo images and automatically brought into coincidence. This does not present any problem in the classical application of stereo triangulation, that is the evaluation of air pictures with well structured ground images. However, with smooth uniform leaves of a plant it is usually difficult to find in two stereo takes pixels which can be uniquely associated with each other. For this reason, the measuring head 20 contains the light pattern projector 25 with which structures can be projected onto the plant as optical marking. Such structures may for example be random dot structures, stripe patterns or grid patterns with good correlation properties, i.e. with pronounced intersection correlation maxima. The light pattern projector may also project uniform light providing adequately structured plant parts are already available. If the patterns required for the stereo measurement interfere with the color classification, two takes are made of each plant, that is a first take with homogeneous white-light illumination for color classification and then a stereo take with pattern projection for stereo triangulation.

For the stereo take two identical cameras are required which are arranged at a defined distance from each other and are directed onto the plant at corresponding angles. In the example described and illustrated it is assumed that one of these two cameras is the color video camera 21, the image signals of which can also be used for the color classification with subsequent form and color evaluation. For this reason the second camera 22 is a color video camera of the same type. This is however not absolutely essential; for stereo triangulation with or without light pattern projection two black-and-white cameras would also suffice. However, in this case as third camera a color video camera would also be additionally necessary for the color classification with subsequent form and color evaluation.

For the evaluation of the stereo images in the height channel the images captured by the two color video cameras 21 and 22 are stored in digitized form in two image memories 70 and 71. For this purpose the image memory 70 can receive the digitized RGB signals from the outputs of the analog-digital converters 41, 42, 43. For the digitizing of the RGB signals furnished by the color video camera 22 a second group of analog-digital converters 72, 73, 74 of the same type is provided, the output signals of which are transmitted to the image memory 71.

The height channel further includes a height computer 75 which evaluates the digitized images stored in the image memories 70 and 71 to determine the height of the plant. For this purpose, the height computer 75 must first find coinciding pixels in the two images; it must then calculate the three-dimensional coordinates of the pixels found and finally it must determine from the calculated coordinates the greatest distance of a pixel from the bottom or the smallest distance of the pixel from the cameras in order to determine the height of the plant. All these steps are known from the application of stereo triangulation in image processing and photogrammetry and therefore do not need to be explained in detail here.

It will only be briefly mentioned that the shift of a plant part between the two stereo images, knowledge of which is necessary in order to determine the height, can be determined on the basis of the projected-on high-frequency pattern in the form of random bright/dark structures by cross-correlation of corresponding image lines along the epipolar line. The epipolar line may be defined as follows: a certain pixel in the image captured by one of the two cameras lies on a ray which passes through the focal point of the objective lens and through the associated object point. This ray is seen by the other camera as line; this line is the epipolar line. The significance of the epipolar line resides in that a certain pixel in one of the two stereo images cannot lie at any point of the other stereo image but only on the epipolar line. The pixel thus need only be sought along the epipolar line. As a result the computing time for finding associated pixel pairs and determining the mutual shift is substantially shortened. The cross-correlation not only makes it possible to detect associated pixel pairs but at the same time by the location of the maximum of the cross-correlation function indicates the mutual shift of the pixels.

In FIG. 4 a further advantageous step is illustrated by which the computing time for finding associated pixel pairs in the digitized stereo images stored in the image memories 70 and 71 can be considerably shortened. For this purpose there is a connection 76 between the form identifying unit 60 and the image computer 65. Via this connection the form identifying unit 60 can report to the height computer 75 image regions which have been identified as belonging to the plant. Since the pixels to be correlated by the height computer 75 must lie in such image regions this considerably restricts the search area which the height computer 75 must investigate in the image memories 70 and 71 for the stereo evaluation. It suffices to report to the height computer 75 information on the image regions of plant parts segmented with the color classification only for the image of one of the two video cameras because it can then easily find the corresponding image regions in the image of the other video camera. In this manner, the color classification made for evaluating form and color features can advantageously also be utilized in the height determination without appreciable additional expenditure.

FIG. 2 shows schematically in the height channel 34 at 34a the two digital stereo images of the plant and of the projected-on light pattern stored in the image memories 70 and 71 and at 34b the plant height h calculated by the height computer 75 from said images.

The control of the light pattern generator 27 by the control and calculating unit 40 permits not only the switching over between uniform light and light pattern projection but also the selection or generation of light patterns which are particularly favourable for the individual use.

As an alternative to the determination of the plant height by stereo triangulation with two cameras, other methods known per se for range or distance measurement may be employed, for example the measuring method on the basis of the light section principle. In this case the light pattern generator 27 is preferably set up for the projection of line structures. This method requires only one camera and a light pattern projector.

If the illumination means 24 is formed by a stroboscopically pulsed light source, the light pulses are likewise triggered by the control and calculating unit 40 as indicated in FIG. 4.

FIG. 5 shows a modified embodiment of the circuit components of FIG. 3. With respect to the embodiment of FIG. 3 the only difference is that the color space converter 44 and the color classifier 50 are united to a combined color space converter and color classifier 80 containing an input multiplexer 82, a table memory 83 and a code converter 54. This embodiment utilizes the fact that in a table memory not only simple associations may be stored but also complex associations obtained by computation from several simple associations. The input multiplexer 82 receives the digitized RGB signals from the outputs of the analog-digital converters 41, 42, 43 and applies these signals to the address inputs $A_0$ to $A_{15}$ of the table memory 83 which contains a memory cell for each combination of digital RGB signals. Directly stored in each memory cell of the table memory 83 is the color class code of the color class converted in the IHS color space and associated with the RGB signal supplied as address. Thus, at an output 81 in the same manner as the color classifier 50 of FIG. 3 the combined color space converter and color classifier 80 supplies to the form identifying unit 60 binary signals which designate the allocation of the consecutively scanned pixels to the image of the plant or to the image of the background, and at an output group 88 supplies to the color identifying unit 65 digital code groups which designate the allocation of the consecutively scanned pixels to plant parts with different color classes. These processes take place under the control of the control and calculating unit 40 via connections 85, 86, 87. The color classes can be learned in the manner described above by the combined color space converter and color classifier 80 by training with the aid of presented image fragments, this not involving any difference for the operator; it is merely necessary to program the control and calculating unit 40 in such a manner that on compiling the table it performs the respective necessary conversion from the RGB color space to the IHS color space.

Of course, various further modifications of the method described and the arrangement for carrying out the method are possible. Thus, in particular the color space converter 45 and/or the color classifier 50 of FIG. 3 or the combined color space converter and color classifier 80 of FIG. 5 can also be implemented by high-speed algorithmic and arithmetic logical units or with neuronal networks.

I claim:

1. A method for automatic optical classification of plants comprising the steps of:
   (a) obtaining an image of a plant with a color video camera;
   (b) digitizing pixelwise the color video signals obtained by the color video camera;
   (c) classifying pixelwise the digitized color video signals in accordance with predetermined color classes, said color classes comprising sets of arbitrarily arranged color vectors to which a respective class code is attributed to under supervised learning on the basis of their belonging to the same meaningful regions;
   (d) segmenting the image of the plant from at least one of the image of the background and the images of different parts of the plant from one another on the basis of the allocation of the pixels of the stored image to the predetermined color classes;
   (e) determining at least one of geometrical form features and color features from at least one of the segmented image of the plant and the segmented images of the plant parts; and
   (f) evaluating at least one of the determined form features and color features for deriving a quality measure.

2. Method according to claim 1, characterized in that the form and/or color features determined are compared with predetermined threshold values and that the quality measure is derived from the comparison result.

3. Method according to claim 1, characterized in that the color classification takes place in a transformed color space.

4. Method according to claim 3, characterized in that the color video camera furnishes RGB signals and that the digitized RGB signals are converted to digital IHS signals.

5. Method according to claim 1, characterized in that from the image of the plant captured by the color video camera the height of the plant is determined by a light section method.

6. Method according to claim 5, characterized in that a light pattern evaluatable by the light section method is projected onto the plant.

7. Method for automatic optical classification of plants comprising:
   acquiring an image of in each case one plant by a color video camera, digitizing pixelwise video signals of the acquired image, storing a digitized image of the plant in an image memory and evaluating the stored digitized image by an image computer for classification of the plant, classifying pixelwise the digitized color video signals prior to storing of the digitized image in accordance with predetermined color classes which are assigned on the one hand to the image of the plant and on the other to the image of the background, effecting the segmentation of the image of the plant from the image of the background on the basis of the allocation of the pixels to the predetermined color classes, determining the segmented image of the plant geometrical form features and evaluating the form features for derivation of a quality measure, the color classification is effected by a color classifier comprising a memory having a plurality of memory cells each of which is allocated to a different color value in the color space, said color classifier being interactively trainable by presentation and said training includes:
   a. erasing the contents of all memory cells of the memory of the color classifier;
   b. displaying the image of a plant captured by the color video camera on a monitor;

c. marking a fragment containing as many pixels as possible of a color class to be identified by the user in the image displayed on the monitor;

d. incrementing in the memory of the color classifier, for each pixel of the marked image fragment the content of the memory cell allocated to the color value of the pixel;

e. designating all the memory cells having contents which due to the incrementations are greater than a predetermined threshold value as belonging to the color class to be identified after the evaluation of all the pixels of the marked image fragment; and f. repeating steps c to e for each further color class to be identified.

8. Method according to claim 7, characterized in that the clusters formed by the designated memory cells in the color space used are subjected to a three-dimensional dilatation with subsequent erosion to close gaps.

9. Method according to claim 7, characterized in that in the incrementation of the content of the memory cell allocated to the color value of a pixel the contents of memory cells allocated to neighbouring color values in the color space used are incremented by amounts which are the smaller the greater the distances of the color values associated with said memory cells from the color value of the pixel.

10. Method according to claim 7, characterized in that a class code is allocated to each color class to be identified and that for designating the allocation of the memory cells to a color class the respective class code is written into each memory cell.

11. Method according to claim 7, characterized in that after the training of the color classifier for each pixel of the segmented image of a plant the memory cell of the image memory allocated to the pixel is designated as belonging to the same color class as the memory cell of the color classifier allocated to the color value of the pixel.

12. A method for automatic optical classification of plants characterized in that:
（a) a stereo image of each plant is captured by means of two color video cameras;

(b) the video signals furnished by each of said two color video cameras and corresponding to the image captured by said color video cameras are digitized pixelwise;

(c) the digitized color video signals corresponding to the image captured by one of said two color video cameras are classified pixelwise in accordance with predetermined color classes which are assigned on the one hand to the image of the plant and on the other to the image of the background;

(d) the segmentation of the image of the plant from the image of the background is effected on the basis of the allocation of the pixels to the predetermined color classes;

(e) from the segmented image of the plant geometrical form features are determined;

(f) each of the digitized stereo images represented by said digitized color video signals are stored in an image memory;

(g) a search is performed in said stored digitized stereo image for associated pixel pairs in search regions which correspond to plant parts which have been segmented by means of said color classification;

(h) the height of said plant parts is determined from the pixels of each pair ascertained by the search; and (i) a quality measure is derived from both said geometrical form features and the heights of said plant parts.

13. Method according to claim 12 characterized in that the stored digitized stereo image is evaluated by the image computer by the method of stereo triangulation.

14. Method according to claim 12 characterized in that a light pattern is projected onto the plant during the taking of the stereo image.

15. Arrangement for automatic optical classification of plants comprising:
(a) two color video cameras arranged at a distance apart and directed onto the plant in such a manner that they capture a stereo image of the plant;

(b) an analog-digital converter arrangement for separately digitizing pixelwise the analog image signals furnished by the one and the other color video camera;

(c) a color classifier for classifying the digitized color video signals corresponding to the image captured by one of said two color video cameras pixelwise in accordance with predetermined color classes which are assigned on the one hand to the image of the plant and on the other hand to the image of the background;

(d) means for effecting the segmentation of the image of the plant from the image of the background on the basis of the allocation of the pixels to the predetermined color classes;

(e) means for determining geometrical form features from the segmented image of the plant;

(f) an image memory for storing the digitized stereo image represented by said digitized color video signals;

(g) a height computer performing a search for associated pixel pairs in the stored digitized stereo image in search regions corresponding to plant parts which have been segmented by means of said color classification and determining the height of said plant parts from the pixels of each pair ascertained by the search; and (h) means for deriving a quality measure from both said geometrical form features and the heights of said plant parts.

16. Arrangement according to claim 15, characterized in that the height computer calculates the height of the plant by the method of stereo triangulation.

17. Arrangement according to claim 15 characterized in that the form identifying unit is connected to the height computer for definition of the search regions.

18. Arrangement according to claim 15 characterized by a light pattern projector which during the acquisition of the stereo image projects a light pattern onto the plant.

19. Arrangement according to claim 18 characterized in that the light pattern projector contains a light pattern generator controllable for generating different light patterns.

20. Arrangement according to claim 19, characterized in that the controllable light pattern generator is a three-dimensional light modulator.

21. Arrangement according to claim 20, characterized in that the three dimensional light modulator consists of a liquid crystal matrix.

22. Arrangement according to claim 19, characterized in that the controllable light pattern generator consists of a power-driven diapositive means.

* * * * *